United States Patent
Speth

(10) Patent No.: US 6,723,876 B2
(45) Date of Patent: Apr. 20, 2004

(54) PROCESS FOR THE INTEGRATED PREPARATION OF AMMONIA AND UREA

(75) Inventor: Christian Speth, Lynge (DK)

(73) Assignee: Haldor Topsoe A/S, Lyngby (DK)

( * ) Notice: Subject to any disclaimer, the term of this patent is extended or adjusted under 35 U.S.C. 154(b) by 385 days.

(21) Appl. No.: 09/952,678

(22) Filed: Sep. 14, 2001

(65) Prior Publication Data

US 2002/0035293 A1 Mar. 21, 2002

(30) Foreign Application Priority Data

Sep. 15, 2000 (DK) ........................... 2000 01371

(51) Int. Cl.$^7$ .................. C07C 273/00; C01G 37/00
(52) U.S. Cl. ................. 564/67; 564/65; 564/69; 423/59
(58) Field of Search .................. 564/69, 65, 67; 423/359

(56) References Cited

U.S. PATENT DOCUMENTS

| | | | |
|---|---|---|---|
| 3,349,126 A | 10/1967 | Hsu et al. .................... | 260/555 |
| 3,684,442 A | 8/1972 | Konoki et al. ............... | 423/359 |
| 4,235,816 A | 11/1980 | Lagana et al. ................ | 564/72 |
| 4,291,006 A * | 9/1981 | Pangani et al. ............. | 423/359 |
| 4,988,491 A * | 1/1991 | Van Dijk et al. ............ | 423/359 |
| 5,523,483 A * | 6/1996 | Singh et al. .................. | 564/68 |

FOREIGN PATENT DOCUMENTS

EP 0905127 A1 * 9/1997

* cited by examiner

Primary Examiner—Johann Richter
Assistant Examiner—J. Parsa
(74) Attorney, Agent, or Firm—Dickstein Shapiro Morin & Oshinsky, LLP

(57) ABSTRACT

Process for the combined preparation of urea and ammonia reactant by steps of providing ammonia synthesis gas containing carbon dioxide and conversion of the synthesis gas to the ammonia reactant, reacting the ammonia reactant with the carbon dioxide in the synthesis gas to ammonium carbamate and to urea product, which process comprises further steps of prior to the conversion of the synthesis gas to the ammonia reactant,
  (i) washing the synthesis gas with an aqueous solution of the ammonia reactant and forming a solution being rich in ammonium carbamate;
  (ii) removing excess of ammonia reactant from the washed synthesis gas by washing with water and withdrawing an aqueous solution of ammonia reactant;
  (iii) purifying the water washed synthesis gas by removing remaining amounts of water and ammonia; and
  (iv) passing the purified synthesis gas to the conversion of the gas to ammonia reactant.

1 Claim, 1 Drawing Sheet

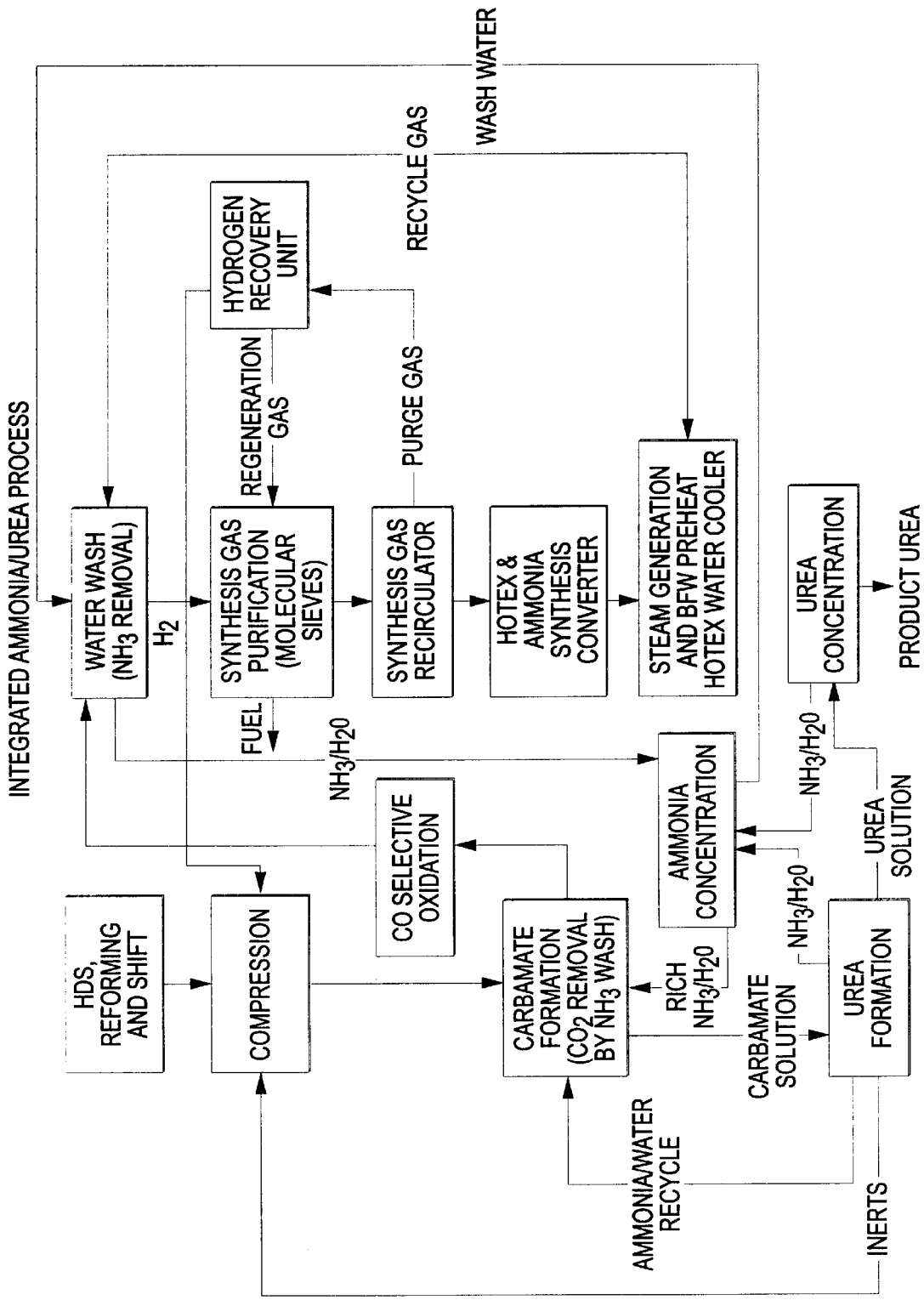

PROCESS FOR THE INTEGRATED PREPARATION OF AMMONIA AND UREA

The present invention is directed towards production of urea by integrating ammonia reactant preparation in the urea synthesis process.

At present urea is made from ammonium carbamate according to the reactions:

$$2NH_3 + CO_2 \text{---} NH_2CO_2NH_4$$

$$NH_2CO_2NH_4 \text{---} H_2O + H_2NCONH_2$$

Most urea is manufactured in connection with synthetic ammonia plants since the necessary carbon dioxide is available from the synthesis gas purification system in front end of the ammonia plant.

A large part of the world's ammonia production is utilized for the manufacture of urea. Thus, an integrated process for production of urea will have technical and economical advantages. However, with the present technology the production of urea and ammonia takes place in largely independent plants.

The general object of this invention is to provide an improved process for the preparation of urea by the above reaction of carbon dioxide with ammonia to ammonium carbamate and carbamate decomposition to urea product, wherein ammonia production and urea production is combined in a single flow scheme by integrating carbon dioxide and ammonia reactant preparation into synthesis gas purification of the ammonia synthesis.

In accordance with the general object, the invention provides a process for the combined preparation of urea and ammonia reactant by steps of providing ammonia synthesis gas containing carbon dioxide and conversion of the synthesis gas to the ammonia reactant, reacting the ammonia reactant with the carbon dioxide in the synthesis gas to ammonium carbamate and to urea product, which process comprises further steps of:

prior to the conversion of the synthesis gas to the ammonia reactant,
(i) washing the synthesis gas with an aqueous solution of the ammonia reactant and forming a solution being rich in ammonium carbamate;
(ii) removing excess of ammonia reactant from the washed synthesis gas by washing with water and withdrawing an aqueous solution of ammonia reactant;
(iii) purifying the water washed synthesis gas by adsorbing remaining amounts of water and ammonia; and
(iv) passing the purified synthesis gas to the conversion of the gas to ammonia reactant.

BRIEF DESCRIPTION OF DRAWING

The attached block diagram describes an integrated process for the preparation of urea from carbon dioxide and ammonia reactant according to a specific embodiment of the invention.

A gas preparation unit consisting of a conventional HDS, Reforming and Shift Section is followed by a unit where the gas with a high $CO_2$ content is brought up to a pressure suitable for ammonia synthesis. The major part of $CO_2$ is then removed by washing the gas with an aqueous ammonia solution. The carbamate solution formed flows to the urea reactor. The dissolved gasses in the solution can from this point be recycled to the suction side of the compressor.

The main flow of stripped gas is now utilised as make-up gas to the ammonia synthesis. First, a CO selective methanisation removes remaining CO. The effluent gas from the methanisation is saturated with $NH_3$ and is mixed with the effluent gas from the ammonia converter. The combined stream is lead to a wash, where ammonia is removed by washing with water. Since this process is exothermal, a two stage process is preferred: In the first stage the gas is in contact with a relative strong ammonia solution, which absorbs about half of the amount of ammonia. In the second stage, the final absorption takes place with water originating from the urea unit.

The gas leaving the absorption unit contains some ammonia, but also some water, which must be removed upstream the ammonia converter. This process may be carried out in a mass absorber by molecular sieves or alumina. The mass absorber can be regenerated by purge gas. Downstream the mass absorber, the gas passes the recirculation compressor and is then passed to a conventional synthesis unit consisting of hot heat exchanger, synthesis converter and steam generation. After cooling to ambient temperature, the gas is passed to water absorption as described above.

Since the carbamate reaction takes place at elevated temperatures and since a large amount of water is formed during the process, it is not required to produce low temperature, anhydrous ammonia for this purpose. Evidently, a too high water content in the produced ammonia will have a negative influence on the urea process, because the water will reduce the yield of urea and thus increase the recycle. Thus, a certain upgrading of the ammonia concentration is required. In the conventional ammonia process there is usually a surplus of low temperature calories which are utilised in the ammonia concentration unit operating at a moderate pressure, typically at 15–17 kg/cm$^2$ g. At this pressure a significant increase in ammonia concentration up to 85% will be obtained by distillation at low temperature, below 120° C.

The process eliminates the need for two compressors (refrigeration and $CO_2$), a refrigeration circuit and a $CO_2$ removal in the ammonia plant. Since the $NH_3$ concentration at converter inlet will be close to nil, a reduction in converter size or a decreased recycle rate is obtained. Large part of the equipment in the urea plant is to recover $CO_2$ and $NH_3$. $CO_2$ is removed by scrubbing with ammonia; water scrubbing and distillation subsequently remove the ammonia. Finally, "inerts" mainly hydrogen and nitrogen are discarded to atmosphere.

By recycling the inert gasses to the suction side of the syngas compressor, a simplification of the process and a reduction of the number of units in the urea plant could be achieved. Further, the urea plant employs a process condensate stripping system that purifies the process water to make it suitable for boiler feed water. In the ammonia plant a similar system is employed and an integration of the two systems may have some potential benefits.

What is claimed is:
1. Process for the combined preparation of urea and ammonia reactant by steps of providing ammonia synthesis gas containing carbon dioxide and conversion of the synthesis gas to the ammonia reactant, reacting the ammonia reactant with the carbon dioxide in the synthesis gas to ammonium carbamate and to urea product, which process comprises further steps of prior to the conversion of the synthesis gas to the ammonia reactant, (i) washing the synthesis gas with an aqueous solution of the ammonia reactant and forming a solution being rich in ammonium carbamate;
(ii) removing excess of ammonia reactant from the washed synthesis gas by washing with water and withdrawing an aqueous solution of ammonia reactant;
(iii) purifying the water washed synthesis gas by removing remaining amounts of water and ammonia; and
(iv) passing the purified synthesis gas to the conversion of the gas to ammonia reactant.

* * * * *